United States Patent [19]

Weaver et al.

[11] Patent Number: 5,208,154

[45] Date of Patent: May 4, 1993

[54] REVERSIBLY IMMOBILIZED BIOLOGICAL MATERIALS IN MONOLAYER FILMS ON ELECTRODES

[75] Inventors: Paul F. Weaver, Golden; Arthur J. Frank, Lakewood, both of Colo.

[73] Assignee: The United States of America as represented by the Department of Energy, Washington, D.C.

[21] Appl. No.: 681,298

[22] Filed: Apr. 8, 1991

[51] Int. Cl.$^5$ ............... C12N 11/14; C12N 11/02; C12N 11/08; C12N 1/02; G01N 27/26

[52] U.S. Cl. ............... 435/176; 435/174; 435/177; 435/261; 435/815; 435/817; 435/180; 204/403

[58] Field of Search ............ 435/817, 176, 174, 177, 435/180, 261, 815; 204/403

[56] References Cited

U.S. PATENT DOCUMENTS

| | | | |
|---|---|---|---|
| 3,839,175 | 10/1974 | Keyes | 204/181 |
| 4,438,196 | 3/1984 | Lantero | 435/96 |
| 4,545,382 | 10/1985 | Higgins et al. | 128/635 |
| 4,563,425 | 1/1986 | Yoshioka et al. | 435/94 |
| 4,572,897 | 2/1986 | Amotz et al. | 435/177 |
| 4,581,336 | 4/1986 | Malloy | 435/176 |
| 4,585,652 | 4/1986 | Miller et al. | 424/83 |
| 4,711,245 | 12/1987 | Higgins et al. | 128/635 |
| 4,798,801 | 1/1989 | Hitzman | 435/167 |
| 4,832,797 | 5/1989 | Vadgama et al. | 204/1 T |
| 4,857,167 | 8/1989 | Bashkin et al. | 204/435 |
| 4,953,552 | 9/1990 | DeMarzo | 128/635 |

OTHER PUBLICATIONS

Fenner et al., (1976) "Medical Virology", 2nd Ed., p. 49, Acad. Press, N.Y.
Brook et al., (1984) "Biology of Microorganisms", 4th Ed., p. 16, Prentice-Hall, Inc., Englewood Cliffs.
Boyd (1984) "General Microbiology", p. 135, Times Mirror/Mosby, Colleg Publishing, St. Louis.

Primary Examiner—David M. Naff
Assistant Examiner—Jon P. Weber
Attorney, Agent, or Firm—Kenneth Richardson; Hugh W. Glenn; William R. Moser

[57] ABSTRACT

Methods and techniques are described for reversibly binding charged biological particles in a fluid medium to an electrode surface. The methods are useful in a variety of applications. The biological materials may include microbes, proteins, and viruses. The electrode surface may consist of reversibly electroactive materials such as polyvinylferrocene, silicon-linked ferrocene or quinone.

7 Claims, 3 Drawing Sheets

FIG. I

REVERSIBLY IMMOBILIZED BIOLOGICAL MATERIALS IN MONOLAYER FILMS ON ELECTRODES

CONTRACTUAL ORIGIN OF THE INVENTION

The United States Government has rights in this invention under Contract No. DE-AC02-83CH10093 between the United States Department of Energy and the Solar Energy Research Institute, a Division of the Midwest Research Institute.

BACKGROUND OF THE INVENTION

1. Field of the Invention

The present invention relates to the reversible immobilization (i.e., attachment) of microbial cells and cell components to solid surfaces through reversible ion-exchange mechanisms.

2. Description of the Prior Art

There are many situations in which intact microbial cells, or cell organelles, or cellular proteins (e.g., enzymes) are of more practical value if they can be immobilized (i.e., attached) on a solid support. Although ion-exchange resins are commercially available for adsorbing organic materials such as microbes and proteins from dilute solutions, the use of such resins results in irreversible binding of lipid-containing materials (such as whole microbial cells and lipoproteins) to the resin. This greatly limits the usefulness and usable lifetimes of such resins.

At neutral pH, cells of different species of bacteria and most proteins have net negative surface charges. Through electrostatic forces, viruses, microbial cells, and anionic proteins can be removed from a suspending medium at neutral pH by use of activated carbon, clay, sand, or anion exchange resins. Although very effective in the removal of biological species, these materials must either be disposed of after use or attempts made to regenerate them by use of concentrated salts, acids or bases. This procedure can be expensive, incomplete, time consuming, and detrimental to the collected species.

U.S. Pat. Nos. 4,832,797 (Vadgama et al.), 4,581,336 (Malloy), 4,572,897 (Amotz et al.), 4,563,425 (Yoshioka et al.), and 4,438,196 (Lantero) describe various techniques for immobilizing enzymes on a substrate. However, none of such patents describes techniques or methods for reversibly binding charged particles on a solid support.

U.S. Pat. No. 4,585,652 (Miller et al.) describes a method for controlled delivery of an ionic bioactive chemical into a physiological medium. The method includes ionically bonding the drug to redox sites within a charged polymer and releasing the drug into the medium by neutralizing the charge on the polymer. The drug molecules are relatively small (molecular weights of a few hundred). This patent does not describe immobilizing relatively large proteins or microbial cells (having molecular weights of several tens of thousands up to a trillion or more) reversibly on the surface of an electrode under a wide range of conditions.

Further, the structure described by Miller et al. involves drug molecules entrapped in the polymer. As a result, there is a diffusion limitation in that the negatively charged drug molecules will either remain entrapped within the polymer matrix (presumably because of steric effects) or they will diffuse slowly out of the polymer.

SUMMARY OF THE INVENTION

It is an object of the present invention to provide a method for reversibly attaching biological materials to the surface of an electrode in a fluid medium.

It is another object of the present invention to provide a method for controlling the adsorption of biological materials on an electrode.

It is yet a further object of this invention to provide a method for reversibly binding a monolayer film of bacteria or enzymes on an electrode.

It is another object of the invention to provide a method for reversibly attaching microbial cells or cell proteins as films on electrodes.

It is yet another object of this invention to provide a method for increasing contact of organic materials in a fluid stream with biological materials attached to an electrode support.

It is another object of this invention to provide a method for obtaining increased bacterial cell or enzyme densities.

To achieve the foregoing and other objects and in accordance with the purpose of the present invention, a method is provided for reversibly binding charged biological particles in a fluid medium to an electrode surface. The method comprises the steps of:

(a) treating (e.g., derivatizing) the electrode surface with an electrochemically active material;
(b) connecting the electrode to an electrical potential; and
(c) exposing the fluid medium to the electrode surface in a manner such that the charged particles become adsorbed on the electrode surface.

To remove the charged particles from the surface of the electrode, the electrical potential is changed so that the charged particles are released from the surface of the electrode.

The present invention provides the ability to control the adsorption of biological materials. Recognizing that virtually all microbes, spores, viruses, and most proteins have a net negative surface charge at neutral pH, the invention provides a method for electrochemically binding such material to positively charged electrodes. The invention employs planar electrode materials that have been coated or derivatized with a thin layer of electrochemically active groups or polymers. When the positive charge of the coated electrode is removed, the organic components, such as spent microbes or enzymes, will be released from the coated surface. The surface is then available for additional cycles of binding and release.

The methods and techniques of this invention are useful in a variety of applications where the enzymatic activity of microbial cells or cell components may be used. The techniques of this invention involve generating or preparing a replaceable monolayer film of bacteria or enzymes, for example, on a solid support.

This then provides a high localized concentration of biological materials which can be placed in direct contact with a flowing fluid stream (i.e., liquid or gas). In this manner the invention provides means for increasing contact of organic materials in the fluid stream with biological materials (e.g., bacteria or enzymes) carried on an electrode support. Because the organic materials flow directly past the solid electrode support, there is close proximity of the biological materials to the organic materials. Also, because the biological materials are retained on the solid electrode support, this arrangement permits increased enzyme or bacterial cell densities and also prevents the biological materials from being diluted by the flowing effluent. It also prevents the flowing effluent from being contaminated with the biological materials. The techniques of the invention also enable the biological materials to be replaced when necessary while retaining the solid electrode support.

Other advantages of the techniques of this invention will be apparent from the following detailed description and accompanying drawings.

DETAILED DESCRIPTION OF THE PREFERRED EMBODIMENTS

In the practice of this invention there is used an electrode surface which has been modified with an electrochemically active material. Nearly all, if not all, microbes, spores, and viruses (and many proteins) have a net negative surface charge at neutral pH because of an excess of free carboxyl and other ionizable groups. They electrostatically bind to positively charged surfaces and are largely unaffected by neutral surfaces. By derivatizing an electrode material with functional groups that are capable of being electrochemically oxidized and reduced (switching from a net positive charge to a neutral or to a net negative charge), biological material can be alternately adsorbed or desorbed.

Figure 1:
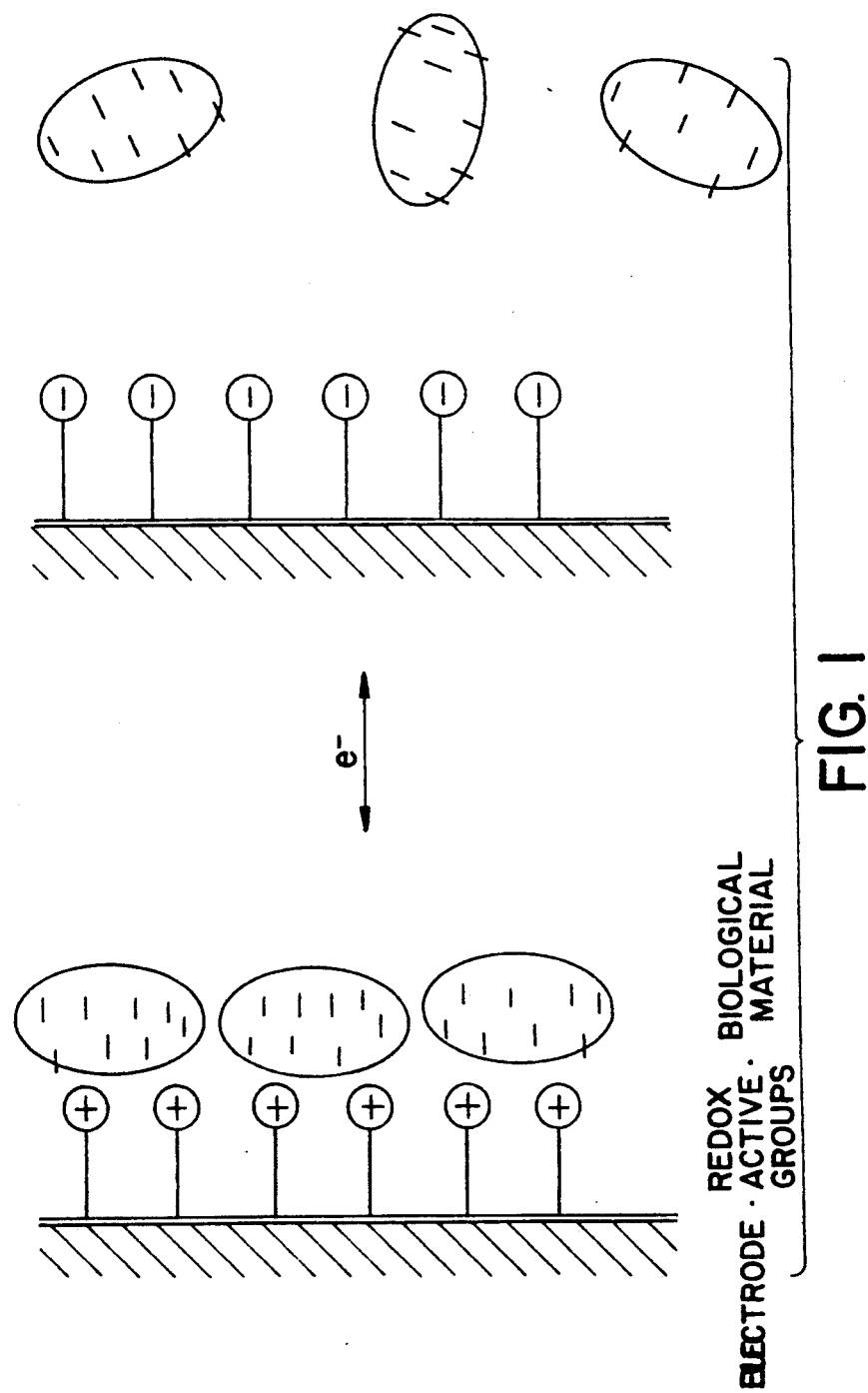
FIG. 1 illustrates reversible binding of bacteria on a planar electrode surface.
Figure 2:
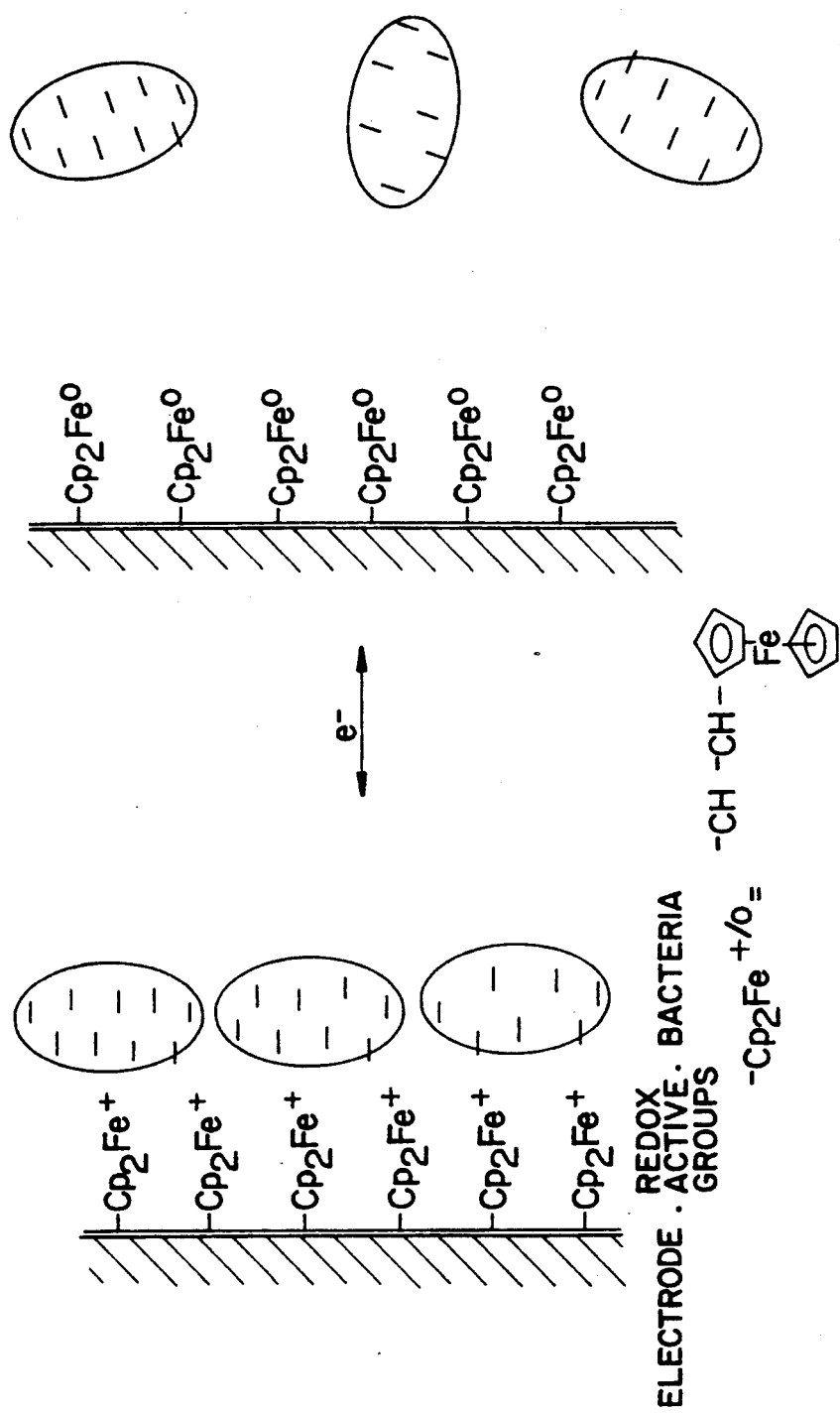
FIG. 2 illustrates immobilization of bacteria on a ferrocene-derivatized electrode surface.

Thus, in the practice of the techniques of this invention, electrode materials are modified with a surface layer of an electrochemically active species, such as ferrocene moieties or a polymer, such as poly(vinylferrocene). In the oxidized state (positively charged) the electroactive groups or electroactive polymers electrostatically bind microbial cells and cell proteins (which are negatively charged). When the groups or polymers are electrochemically reduced to a neutral or negatively charged state, the biological components are released from the electrode surface. This is illustrated in FIGS. 1 and 2.

Figure 3:
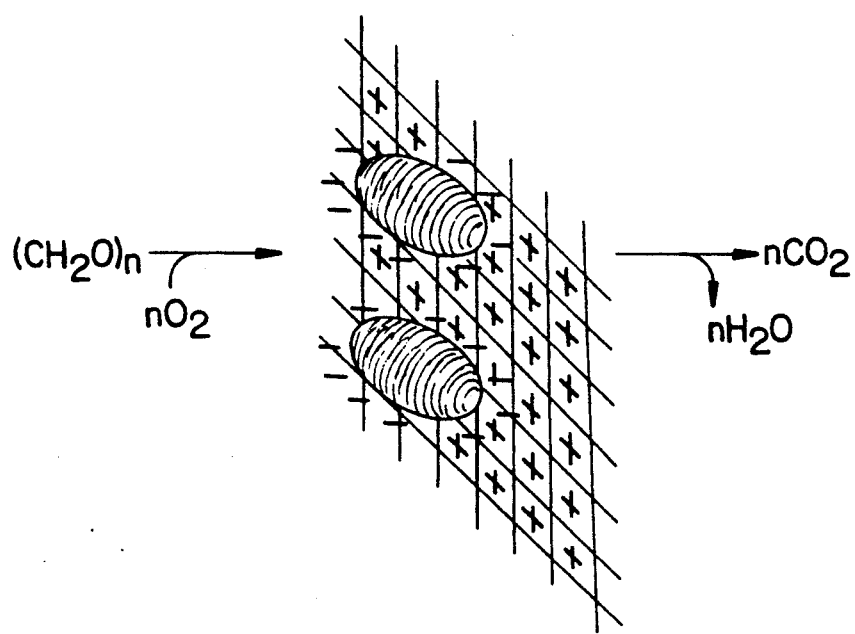
FIG. 3 illustrates oxidative removal of organic materials from a liquid or gaseous stream using reversibly immobilized microbes.

The invention offers potential for use in applications where it is necessary or desirable to reversibly bind charged biological particles or materials to an electrode surface. FIG. 3 illustrates use of the techniques of the invention in the oxidative removal of organic materials from a fluid stream (e.g. water).

Conductive carbon and tin oxide-coated glass have been found to be the preferred materials for the electrode in this invention. Derivatization of the surface of the electrode involves attaching redox groups. Silane coupling agents are very useful in facilitating attachment of redox materials to the electrode surface.

Preferred materials for derivatizing the electrode surface are electroactive groups or electroactive polymers which can be electrochemically cycled between charged states. These electroactive groups or electroactive polymers are stable in air and common fluids (such as water) and can transport charges.

In their charged state, these electroactive groups and electroactive polymers are capable of attracting and retaining oppositely-charged chemical species such as biological materials. The ionically-bound biological materials can be released when the positively charged electrode surface is neutralized or acquires a net negative charge. The coatings of electroactive groups or electroactive polymers include those having localized redox sites such as silicon-linked ferrocene or adsorbed or chemically attached polymer such as poly(vinylferrocene). Useful polymers are also described in U.S. Pat. No. 4,585,652, incorporated herein by reference.

The methods of the invention have been found to be useful in reversibly adsorbing biological materials to electrode surfaces through electrostatic interactions. Most proteins and nearly all microbial cells have a net negative surface charge at neutral pH and adsorb onto positively charged surfaces though not onto negatively charged surfaces. In the bound state, many enzymes may increase their functional lifetimes by several orders of magnitude but still need a method of replacement if the entire electrode-enzyme complex is not to be discarded. Biological materials can be bound to positively charged electrode surfaces derivatized with electrochemically active groups and subsequently released when the redox groups are reduced, causing a net neutral or net negative surface charge on the electrode. The renewed surface is then able to bind new biological material when the surface is reoxidized.

The present invention establishes the feasibility of reversibly binding biological materials onto a substrate using only electrostatic forces created by attaching redox species to the surface of the substrate. After binding and subsequent release from the surface, both bacteria and enzymes retain their activity. The method is simple in concept and in practice and has the significant advantage over ion-exchange resins for reversibly binding biological materials without introducing chemicals, buffers or salts into the system. Additionally, lipid-containing materials perform similarly.

The invention is further illustrated by means of the following non-limiting examples.

EXAMPLE 1

Polyvinylferrocene-coated planar tin oxide electrodes bound several species of bacteria from liquid aqueous suspensions within 30 seconds after applying a potential of 0.6 V (vs. SCE). The bacteria remained stably adsorbed on the surface when washed with sterile water. Calculations based on spectral measurements of the bacteriochlorophyll content of the adsorbed bacteria indicated that about 57% of the electrode surface was covered by bacterial cells. See Table I. Changing the applied potential to 0.0 V reduced the ferrocene, removing the net positive surface charge on the electrode, and released about 60% of the adsorbed bacteria. X-ray photoelectron spectroscopy analysis indicated that there was only one ferrocene for each 160 carbons in the polymer backbone, which may have provided sufficient hydrophobic binding sites to prohibit complete release of the remaining bacteria.

As a comparative example, polypyrrole (a conductive polymer described in U.S. Pat. No. 4,585,652) was used on the electrode surface in place of polyvinylferrocene. Although bacteria were attached on about 88% of the electrode surface, following the procedure of Example 1, testing revealed that 0% of the bacteria were released. Thus, this established that the conductive polymer (polypyrrole) entrapped the bacteria irreversibly.

EXAMPLE 2

Before derivatization, tin oxide conducting glass electrodes were cleaned by ultrasonicating them in distilled water for 5 minutes and then in dichloromethane for 10 minutes. The electrodes were next dried under a $N_2$ stream (99.999% pure). The method for chemically modifying the electrode surface with ferrocene was similar to that used by J. R. Lenhard and R. W. Murray, J. Am. Chem. Soc. 100, 7870 (1978).

The attachment of ferrocene groups to the tin oxide electrode surface involved the surface reaction of Sn—OH with the alkylaminesilane 3-aminopropyltrimethoxysilane to form surface amine groups. This was followed by a carbodiimide-assisted amidization of ferrocenecarboxylic acid. More specifically, the cleaned electrode was heated in purified air at 450° C. for several hours to promote formation of Sn—OH surface groups. The electrode was next refluxed in a 10% solution of the silanating agent in dry benezene for 5 hours and then rinsed alternatingly (under $N_2$) with benzene and $CH_3CN$. This silanized surface was then refluxed for 24 hours in $CH_3CN$ solution containing 100 mg ferrocenecarboxylic acid and 200 mg 1,3-dicyclohexylcarbodiimide (DCC). The chemically modified electrode was rinsed with $CH_3CN$ and then ultrasonicated in $CH_3CN$. The entire chemical modification was carried out under highly pure $N_2$. Binding of bacteria to the oxidized surface was poor, although the subsequent release of bound bacteria was as high as 90%. See Table I.

EXAMPLE 3

Other electrodes were derivatized in a similar manner with silicon-linked quaternary amines in order to provide a fixed positive charge on the surface. The tin oxide conducting glass was cleaned in methanol or chloroform by ultrasonication for 0.5 hours. Following silanation, the electrode was refluxed for 24 hours in dry benzene (under $N_2$) containing $(CH_3)_2N(CH_2)_3OH$ and a 5-fold excess of DCC. It was rinsed repeatedly in dry benzene under $N_2$ and then refluxed overnight in absolute methanol containing 10% $CH_3I$ resulting in quaternary amine formation. An electrochemically active hydrophobic quinone was then adsorbed onto the surface by repeated dipping and drying. This quinone was the DCC ester of benzoquinone. The rationale for using a two-electron accepting benzoquinone as the electroactive group was that its reduction to the hydroquinone state would produce anionic charges strong enough to repel the negatively charged bacteria away from the surface. Some electrode preparations bound bacteria over about 50% of their surface with nearly total release and could be cycled several times. See Table I. Optical photomicrographs of the electrode surface indicate that bacterial adsorption and desorption could be made to occur repetitively by cycling electrochemically.

TABLE I

Adsorption of Bacteria to, and Desorption from, Electrochemically Active Electrode Surfaces

| Electrode Derivative | % surface covered by bacteria | % bacteria released from surface |
|---|---|---|
| Example 1: Polyvinylferrocene: | | |
| oxidized | 57 | |
| reduced | 22 | 60 |
| Example 2: Si-Linked Ferrocene | | |
| oxidized | 10 | |
| reduced | 1 | 90 |
| Example 3: Si-Linked Quaternary Amine/Quinone: | | |
| oxidized | 53 | |
| reduced | <1 | 98 |

The foregoing is considered as illustrative only of the principles of the invention. Further, since numerous modifications and changes will readily occur to those skilled in the art, it is not desired to limit the invention to the exact construction and operation shown and described. Accordingly, all suitable modifications and equivalents may be resorted to falling within the scope of the invention as defined by the claims which follow.

The embodiments in which an exclusive property or privilege is claimed are defined as follows:

1. A method for reversibly binding negatively charged biological particles in a liquid medium at neutral pH to an electrode surface, wherein said particles are selected from the group consisting of microbial cells and proteins the method comprising the steps of:
   (a) treating said electrode surface with an electrochemically active material selected from the group consisting of polyvinylferrocene, silicon-linked ferrocene and quinone;
   (b) connecting said electrode to an electrical potential; wherein said electrical potential induces a positive charge on said electrochemically active material; and
   (c) exposing said medium to said electrode surface in a manner such that said charged particles are adsorbed on said electrode surface.

2. A method in accordance with claim 1, comprising the further step of changing said electrical potential to cause release of said particles from said electrode surface.

3. A method in accordance with claim 1, wherein said liquid comprises water.

4. A method in accordance with claim 1, wherein said electrode surface is planar.

5. A method in accordance with claim 1, wherein said electroactive material consists of polyvinylferrocene or silicon-linked ferrocene.

6. A method in accordance with claim 1, wherein said electrode surface is made of a material that is selected from the group consisting of tin oxide-coated glass and carbon.

7. A method in accordance with claim 3, wherein said charged particles comprise proteins.

* * * * *